United States Patent [19]

Roling

[11] Patent Number: 5,023,372

[45] Date of Patent: Jun. 11, 1991

[54] METHODS AND COMPOSITIONS FOR INHIBITING (METH)ACRYLIC ACID POLYMERIZATION

[75] Inventor: Paul V. Roling, Spring, Tex.

[73] Assignee: Betz Laboratories, Inc., Trevose, Pa.

[21] Appl. No.: 352,579

[22] Filed: May 16, 1989

[51] Int. Cl.$^5$ .............................................. C07C 57/075
[52] U.S. Cl. ........................................ 562/598; 560/4; 252/400.53; 252/401
[58] Field of Search ........................... 562/598; 560/4; 252/400.53, 401; 558/639

[56] References Cited

U.S. PATENT DOCUMENTS

| | | | |
|---|---|---|---|
| 3,893,895 | 7/1975 | Dehnert et al. | 203/59 |
| 4,507,495 | 3/1985 | Dougherty et al. | 560/205 |
| 4,638,079 | 1/1987 | Inskip et al. | 560/4 |
| 4,663,480 | 5/1987 | Inskip et al. | 562/598 |
| 4,720,566 | 1/1988 | Martin | 558/306 |
| 4,797,504 | 1/1989 | Roling | 560/4 |
| 4,912,247 | 3/1990 | Roling | 558/306 |

FOREIGN PATENT DOCUMENTS 51-98211  8/1976  Japan .

*Primary Examiner*—Jose G. Dees
*Attorney, Agent, or Firm*—Alexander D. Ricci; Bruce E. Peacock

[57] ABSTRACT

Methods and compositions are provided for inhibiting the polymerization of acrylic acid monomers during elevated temperature processing thereof or during storage or shipment of acrylic acid product. The compositions comprise a combination of a Mn source compound and a phenylenediamine compound having at least 1 N-H bond. The methods comprise adding from about 1-10,000 ppm of the combination to the particular acrylic acid containing medium for which such antipolymerization protection is desired, per million parts of the acrylic acid medium.

13 Claims, No Drawings

METHODS AND COMPOSITIONS FOR INHIBITING (METH)ACRYLIC ACID POLYMERIZATION

FIELD OF THE INVENTION

The present invention pertains to methods and compositions for inhibiting the undesired polymerization of (meth)acrylic acid monomers during processes such as monomer preparation, and purification, and during storage and shipment of products containing such monomers.

BACKGROUND OF THE INVENTION

Polymerizable (meth)acrylic acids undesirably polymerize during various stages of the manufacturing, processing, handling, storage and use thereof. One especially troublesome problem is the polymerization of (meth)acrylic acid monomer in the purification stages of monomer production. It is well known that the monomers readily polymerize and that such polymerization increases with concurrent temperature increases.

Common industrial methods for producing (meth)acrylic acids include a variety of purification processes, including distillation, to remove impurities. Unfortunately, purification operations carried out at elevated temperatures result in an increased rate of undesired polymerization. Polymerization, such as thermal polymerization, during the monomer purification process, results not only in loss of desired monomer end-product, but also in loss of production efficiency caused by polymer formation or agglomeration on process equipment. In heat requiring operations, such agglomeration adversely affects heat transfer efficiency.

PRIOR ART

A variety of compositions and methods have been proposed for inhibiting uncontrolled polymerization of (meth)acrylic acid and esters. Known inhibitors include phenothiazine, methylene blue, hydroquinone, hydroquinone methyl ether (MEHQ) and sundry manganese containing compounds.

In U.S. Pat. No. 4,797,504 (of common inventorship and assignment herewith), hydroxylamines and phenylenediamines, in combination, are taught as being effective anti-polymerization aids for acrylate monomer systems. This particular combination has also been shown to be effective in inhibiting acrylonitrile polymerization in U.S. Pat. No. 4,720,566 (Martin)—of common assignment herewith.

Japanese patent publication 51-98211 teaches that polymerization of $\alpha,\beta$ unsaturated carboxylic acids can be inhibited by the use of sundry manganese salts, with or without hydroquinone or MEHQ, save for the particular sodium manganese ethylene diamine tetra-acetate salt. Similarly, in U.S. Pat. No. 4,507,495 (Dougherty et al.) acrylic acid polymerization is inhibited in ethyl acrylate production methods by the use of manganese or cerium salts that are soluble in the reaction mixture. Manganese nitrite, $Mn(NO_2)_2$, is used as a polymerization inhibitor in U.S. Pat. No. 4,663,480 (Inskip et al.).

Of somewhat lesser importance is U.S. Pat. No. 4,638,079 (Inskip et al.) which discloses processes for inhibiting polymerization of polymerizable ethylenically unsaturated monomers such as hydrocarbons, acids and esters wherein a cobalt (III), nickel (II), or manganese (II) complex of N-nitrosophenylhydroxylamine is utilized. In a preferred embodiment of the '079 disclosure, polymerization of an acrylic acid or acrylate ester is inhibited.

Despite the prior art efforts, there remains a need in the art for an effective (meth)acrylic acid polymerization inhibitor. Moreover, such an inhibitor that is environmentally less suspect than conventional inhibitors such as phenothiazine is highly desirable.

Further, it is desirable to provide a low volatility anti-poymerization treatment so that the treatment will not be carried overhead with the purified monomer during the distillation (i.e., purification) thereof.

There is an even more specific need for an acrylate anti-polymerization treatment that is readily soluble in non-polar organic solvents, such as xylene or heavy aromatic naphtha, so that the treatment can be dissolved therein and provide a stable product that can be shipped and stored without undue fear of product deterioration and separation.

These and other needs in the art are addressed by the methods and compositions detailed herein.

DETAILED DESCRIPTION OF THE PREFERRED EMBODIMENT

In accordance with the invention, both a phenylenediamine compound and a manganese salt are conjointly used to provide effective inhibition of polymerization of polymerizable acrylic acid monomers. The phrase "acrylic acid monomers" as herein used is intended to include acrylic acid, methacrylic acid, crotonic acid and isocrotonic acid.

As to the phenylenediamines that may be used, these include the phenylenediamines having at least one N—H bond. It is thought that o-phenylenediamine or derivatives thereof having at least one N—H bond are suitable in accordance with the instant invention.

However, the preferred phenylenediamines are the p-phenylenediamines having the structure

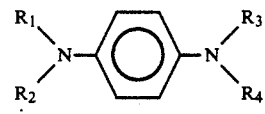

wherein R1, R2, R3, and R4 are the same or different and are hydrogen, alkyl, aryl, alkaryl, or aralkyl groups with the proviso that at least one of R1, R2, R3, or R4 is hydrogen. More preferably, the alkyl, aryl, alkaryl, and aralkyl groups have one to about twenty carbon atoms. The alkyl, aryl, alkaryl, and aralkyl groups may be straight or branched-chain groups. Exemplary p-phenylenediamines include p-phenylenediamine wherein R1, R2, R3, and R4 are hydrogen; N-phenyl-N'-alkyl-p-phenylenediamines such as, N-phenyl-N'-methyl-p-phenylenediamine, N-phenyl-N'-ethyl-p-phenylenediamine, N-phenyl-N'-n-propyl-p-phenylenediamine, N-phenyl-N'-isopropyl-p-phenylenediamine, N-phenyl-N'-n-butyl-p-phenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine; N-phenyl-N',N'-dialkyl-p- phenylenediamines such as N-phenyl-N', N'-dimethyl-p-phenylenediamine, N-phenyl-N', N'-diethyl-p-phenylenediamine, N-phenyl-N', N'-di-n-butyl-p-phenylenediamine, N-phenyl-N', N'-di-sec-butyl-p-phenylenediamine, N-phenyl-N'-methyl-N'-ethyl-p-phenylenediamine; N,N-dialkyl-p-phenylenediamines such as N,N-dimethyl-p-phenylenediamine, and N,N-diethyl-p-phenylenediamine; N,N'-dialkyl-p-phenylenediamines such as N,N'-dimethyl-p-phenylenediamine, N,N'-diethyl-p-phenylenediamine, and N,N'-di-isopropyl-p-phenylenediamine; N,N'-diaryl-p-phenylenediamines such as N,N'-diphenyl-p-phenylenediamine: N,N,N'-trialkyl-p-phenylenediamines such as N,N,N'-trimethyl-p-phenylenediamine, and N,N,N'-triethyl-p-phenylenediamine. Preferably, the p-phenylenediamine is selected from the group consisting of N-phenyl-N'-(1,3-dimethylbutyl)-p-phenylenediamine and N-phenyl-N'-(1,4-dimethylpentyl)-p-phenylenediamine.

Any source of manganese can be used as long as it is compatible with the acrylic acid reaction medium. Preferably, the manganese source is a compound that is soluble in non-polar organic solvents such as xylene and heavy aromatic naphtha (HAN so that the combined manganese compound-phenylenediamine treatment may be dissolved in such solvent to provide a stable product.

Preferred manganese source compounds include the manganese salts of $C_1$-$C_{30}$ carboxylic acids such as the formate, acetate, propionate, butyrate, and octanoate salts and the Mn salts of fatty acids such as the naphthenate, tallate and stearate salts. The use of $C_4$-$C_{20}$ manganese salts of carboxylic acids is even more specifically preferred. At present, the most preferred Mn source is manganese naphthenate. As used herein, "Mn source" is defined as a manganese containing compound or complex that will contribute manganese in the acrylic acid reaction mixture to help in impeding polymerization, such as thermal polymerization, of the monomer.

Other exemplary Mn sources include manganese nitrite, manganese acrylate, manganese methacrylate, manganese naphthalate, manganese sulfate, manganese nitrate, manganese carbonate, manganese oxide, manganese hydroxide, manganese chloride, and manganese phosphate.

The total amount of manganese compound plus phenylenediamine or derivatives thereof having at least one N—H group used in the methods of the present invention as a polymerization inhibitor is that amount which is sufficient to effect inhibition of polymerization and will, of course, vary according to the conditions under which the monomer is synthesized, processed, and/or stored. At higher temperatures, larger amounts of the anti-polymerization treatment are generally required. Preferably, the total amount of combined treatment (i.e., manganese compound plus phenylenediamine or derivative thereof having at least one N—H group) is from about 1 ppm to about 10,000 ppm combined treatment based on the weight of the acrylic acid monomer. Most preferably, the total amount of the aforesaid compounds is from 5 ppm to about 1,000 ppm based on the weight of the acrylate monomer. The weight ratios of manganese (as metal) to phenylenediamine or derivatives thereof having at least one N—H group are preferably in the range of about 0.05:1 to about 2.5:1. Most preferably, the weight ratio of manganese (as metal) to phenylenediamine or derivative thereof having at least one N—H group is about 0.1:1 to 1:1.

The method of the present invention can control the fouling of processing equipment, such as the equipment used in separation and purification processes of acrylic acid monomer, which is due to or caused by the polymerization of the monomer. The instant invention may be used as both a process inhibitor, which is employed during preparation and processing (e.g., employing heat) of the acrylic acid or methacrylic acid at elevated temperatures, and as a product inhibitor, which is combined with the acrylic acid or methacrylic acid in order to inhibit polymerization during storage and handling. The manganese compound plus phenylenediamine or derivative thereof having at least one N—H group can be added to the acrylic acid or methacrylic acid by any conventional method. The components can be added to the acrylic acid or methacrylic acid as a single composition containing the inhibitor compounds or the individual components can be added separately or in any other desired combination. It is clearly preferred to add the composition as a single treatment composition comprising both of the active acrylic acid anti-polymerization components.

The composition may be added as either a dispersion or as a solution using a suitable liquid carrier dispersing medium or solvent which is compatible with the acrylic acid or methacrylic acid. Preferably, a solution is provided and the solvent is a non-polar organic solvent such as xylene (a commercial mixture of o, m, and p isomers), or heavy aromatic naphtha.

Based upon presently available data, the composition preferred for use is a Mn naphthenate and N-phenyl-N'(1,4-dimethylpentyl)-p-phenylenediamine (PDP) combination in a 0.5:1 weight ratio of components dissolved in heavy aromatic naphtha. Optimal dosage rates for the compositions are on the order of from about 5-1000 ppm of the combined manganese compound (as Mn) and phenylenediamine compound per one million parts of the acrylic acid monomer for which polymerization inhibition is desired.

The data set forth below were developed and demonstrate the unexpected results occasioned by use of the invention. The following examples are included as being illustrations of the invention and should not be construed as limiting the scope thereof.

EXAMPLES

N-Phenyl-N'-(1,4-dimethylpentyl)-p-phenylenediamine was the exemplary phenylenediamine used in the following examples and is designated as "PDP".

Manganese naphthenate, supplied as a 6% solution of manganese, was the exemplary manganese compound used in the following examples.

Evaluation of the inhibitors was carried out using acrylic acid. Acrylic acid was distilled under vacuum, with the portion distilling at about 35°-40° C./5 torr being used, to remove the majority of MEHQ inhibitor contained in the acrylic acid.

In a 17-mL test-tube was placed 5.0 mL of the distilled acrylic acid and the appropriate amount of inhibitor (in a 0.02 weight/volume % solutions in xylene). The tube was sealed with a tight fitting septum cap. A 9-inch long, 4-mm diameter soft glass tube closed at the bottom and partly filled with mineral oil was inserted through the septum to the bottom of the test-tube. A thermocouple was then placed in the 4-mm tube and the whole set-up placed in an oil bath kept at a temperature of about 294° or 224° F. The temperature of the sample was monitored on a datalogger with the time for the exothermic polymerization reaction being noted. Exotherms for samples were sharp and large, with peak temperatures being about 400° F.

All examples were conducted with air present in the tube, except Example 8 where argon was purged through the tubes for 50 seconds. The butyl acrylate of Example 8 was double distilled under vacuum to remove MEHQ.

Generally, a set of ten samples was conducted at one time. Exotherm times varied from set to set, possibly depending on the efficiency of the distillation for removing the MEHQ.

EXAMPLE 1

In this example, various amounts of manganese and of PDP were added to the acrylic acid. In the controls, where neither manganese nor PDP was used, the acrylic acid polymerized in 4-5 minutes as indicated by the exotherm. In this example and in the other examples with acrylic acid only, the addition of PDP alone did not significantly increase inhibition time versus the controls. As the amount of manganese alone was increased, the inhibition time decreased (Table I).

However, the use of the combination of manganese and PDP showed at least double the inhibition of polymerization versus that found for the manganese alone (Table I).

TABLE I

Acrylic Acid Polymerization Data at 294° F. Bath

| Manganese (ppm) | PDP (ppm) | Minutes to Exotherm | Mn/PDP |
|---|---|---|---|
| 0 | 0 | 4, 4, 5, 5 | — |
| 0 | 20 | 6 | 0 |
| 1 | 0 | 27 | — |
| 1 | 20 | 43 | 0.05 |
| 3 | 0 | 23 | — |
| 3 | 20 | 92 | 0.15 |
| 5 | 0 | 32, 33 | — |
| 5 | 10 | 83 | 0.5 |
| 5 | 20 | 89, 77, 139 | 0.25 |
| 10 | 0 | 13 | — |
| 10 | 20 | 140 | 0.5 |
| 25 | 0 | 2 | — |
| 25 | 20 | 144 | 1.25 |

EXAMPLE 2

The first part of this example shows the excellent inhibition by the combination of manganese and PDP over the individual components. In the second part of this example, the addition of stainless steel wire lowered all exotherm times, but the combination of manganese and PDP was still excellent (Table II).

TABLE II

Acrylic Acid Polymerization Data at 294° F. Bath

| Manganese (ppm) | PDP (ppm) | Minutes to Exotherm | Mn/PDP |
|---|---|---|---|
| 0 | 0 | 5 | — |
| 0 | 20 | 6 | 0 |
| 5 | 0 | 24 | — |
| 10 | 20 | 122 | 0.5 |
| with .20 g 316 stainless steel wire added | | | |
| 0 | 0 | 3 | — |
| 0 | 20 | 5 | 0 |
| 5 | 0 | 16 | — |
| 10 | 20 | 76 | 0.5 |

EXAMPLE 3

At the lower bath temperatures, exotherm times were increased and the combination of manganese and PDP was at least twice as great as the manganese alone. PDP alone did not significantly extend the exotherm (Table III).

TABLE III

Acrylic Acid Polymerization Data at 224° F. Bath

| Manganese (ppm) | PDP (ppm) | Minutes to Exotherm | Mn/PDP |
|---|---|---|---|
| 0 | 0 | 32 | — |
| 0 | 20 | 56 | 0 |
| 5 | 0 | 5,436 | — |
| 5 | 20 | 16,209 | 0.25 |
| 10 | 0 | 238 | — |
| 10 | 20 | >30,240 | 0.5 |
| 25 | 0 | 7 | — |
| 25 | 10 | 11,300 | 2.5 |
| 25 | 20 | ~11,300 | 1.25 |

EXAMPLE 4

This example again shows the excellent inhibiting properties of the manganese and PDP combination (Table IV).

TABLE IV

Acrylic Acid Polymerization Data at 294° F. Bath

| Manganese (ppm) | PDP (ppm) | Minutes to Exotherm | Mn/PDP |
|---|---|---|---|
| 0 | 0 | 4 | — |
| 0 | 20 | 8 | 0 |
| 5 | 0 | 78 | — |
| 10 | 20 | 188 | 0.5 |
| 0 | 0 | 5 | — |
| 5 | 0 | 32 | — |
| 5 | 20 | 90 | 0.25 |
| 5 | 40 | 174 | 0.125 |
| 5 | 60 | 292 | 0.0825 |

EXAMPLE 5

This example shows the excellent inhibiting properties of the manganese and PDP combination at 294° F. One experiment, wherein the weight ratio of manganese to PDP was 5:1, shows the detrimental effects of too much manganese in relation to the PDP (TABLE V).

TABLE V

Acrylic Acid Polymerization Data at 294° F. Bath

| Manganese (ppm) | PDP (ppm) | Minutes to Exotherm | Mn/PDP |
|---|---|---|---|
| 0 | 0 | 6, 5, 5, 6 | — |
| 0 | 5 | 5, 5 | 0 |
| 0 | 10 | 6, 5, 5, 5 | 0 |
| 1 | 0 | 10 | — |
| 1 | 5 | 18, 17 | 0.2 |
| 1 | 10 | 22, 21 | 0.1 |
| 2 | 0 | 16, 12 | — |
| 2 | 2 | 16 | 1.0 |
| 2 | 5 | 21, 21 | 0.4 |
| 2 | 10 | 42, 45, 25 | 0.2 |
| 5 | 0 | 9 | — |
| 5 | 5 | 16 | 1.0 |
| 5 | 10 | 27 | 0.5 |
| 10 | 0 | 3, 8, 3 | — |
| 10 | 10 | 22 | 1.0 |
| 10 | 2 | 3 | 5.0 |

EXAMPLE 6

This example again shows the excellent inhibiting properties of the manganese and PDP combination at 224° F. (TABLE VI).

TABLE VI

| Acrylic Acid Polymerization Data at 224° F. Bath | | | |
|---|---|---|---|
| Manganese (ppm) | PDP (ppm) | Minutes to Exotherm | Mn/PDP |
| 0 | 0 | 57, 51 | — |
| 0 | 5 | 170 | 0 |
| 5 | 0 | 26 | — |
| 5 | 5 | >3180 | 1.0 |

EXAMPLE 7

In this example, the weight ratios of manganese to PDP are outside the limits of this invention. The combinations of manganese and PDP do not show inhibition greater than that of the manganese alone (TABLE VII).

TABLE VII

| Acrylic Acid Polymerization Data at 224° F. Bath | | | |
|---|---|---|---|
| Manganese (ppm) | PDP (ppm) | Minutes to Exotherm | Mn/PDP |
| 0 | 0 | 39, 39 | — |
| 0 | 2 | 21 | 0 |
| 0 | 4 | 18 | 0 |
| 0 | 6 | 19 | 0 |
| 0 | 10 | 41, 72 | 0 |
| 0.025 | 0 | 64 | — |
| 0.025 | 2 | 73 | 0.0125 |
| 0.025 | 4 | 55 | 0.00825 |
| 0.025 | 6 | 43 | 0.00417 |
| 0.050 | 0 | 76 | — |
| 0.4 | 0 | >126 | — |
| 0.4 | 10 | >126 | 0.04 |
| 0 | 0 | 168 | — |
| 0.1 | 0 | >423 | — |
| 0.1 | 10 | 360 | 0.01 |

EXAMPLE 8

When 2, 5, 10 or 20% of acrylic acid was mixed with butyl acrylate, the combination of manganese and PDP showed greater inhibition than either manganese or PDP alone and greater inhibition than the sum of the individual manganese and PDP experiments (Table VIII).

TABLE VIII

| Acrylic Acid Polymerization Data at 294° F. Bath | | | |
|---|---|---|---|
| Percent Acrylic Acid in Butyl Acrylate | Manganese (ppm) | PDP (ppm) | Minutes to Exotherm |
| 20 | 0 | 0 | 9 |
| 20 | 0 | 20 | 10 |
| 20 | 5 | 0 | 26 |
| 20 | 5 | 20 | >289 |
| 10 | 0 | 0 | 11 |
| 10 | 0 | 20 | 17 |
| 10 | 5 | 0 | 5 |
| 10 | 5 | 20 | 326 |
| 5 | 0 | 0 | 9 |
| 5 | 0 | 20 | 39 |
| 5 | 5 | 0 | 5 |
| 5 | 5 | 20 | 298 |
| 2 | 0 | 0 | 7 |
| 2 | 0 | 20 | 74 |
| 2 | 5 | 0 | 5 |
| 2 | 5 | 20 | 119 |
| 0 | 0 | 0 | 5,5 |
| 0 | 0 | 20 | 972,1162 |
| 0 | 5 | 0 | 27,27 |
| 0 | 5 | 20 | 109,104 |

In accordance with the above, it is shown that the phenylenediamine (PDA) and Mn source compound combined treatment, having a weight ratio of $MN^{++}$:PDA of about 0.05:1 to about 2.5:1, provides better anti-polymerization efficacy at elevated temperatures than the sum of the treatment efficacies provided by individual components of the combination at the same temperatures. Accordingly, it is therefore possible to produce a more effective acrylic acid monomer anti-polymerization treatment than is obtainable by the use of either individual ingredient alone when measured at comparable treatment levels. Because of the enhanced polymerization inhibiting activity of the mixture, the concentration of each of the ingredients may be lowered and the total quantity of the polymerization inhibitor required for an effective treatment at elevated temperatures may be reduced. This factor is especially important in monomer purification procedures where the obvious goal of the process is to provide high level monomer purity.

The term "elevated temperatures" as used herein means temperatures of from about 100°-300° F. that are commonly utilized during the heat treatment of the acrylic acid monomers. Such heat treatment processes include distillation and sundry other procedures.

The methods and compositions of the present invention can control the fouling of processing equipment, such as equipment used in the separation and purification processes of acrylic acid monomers, which is due to or caused by the polymerization of the monomers. The instant invention is useful as a process inhibitor, which is employed during the heat treatment preparation and processing of the monomer at elevated temperatures. The invention can be utilized under normal pressure (760 mm), under superatmospheric pressure or under reduced pressure. The Mn source compound and phenylenediamine or derivatives thereof can be provided to the acrylic acid monomer by any conventional method. The components can be added to the monomer as a single composition containing the inhibitor compounds or the individual components can be added separately or in any other desired combination.

While this invention has been described with respect to particular embodiments thereof, it is apparent that numerous other forms and modifications will be obvious to those skilled in the art. The appended claims generally should be construed to cover all such obvious forms and modifications which are within the true spirit and scope of the present invention.

I claim:

1. A method of inhibiting acrylic acid monomer polymerization comprising adding to the monomer an effective inhibiting amount of (a) a manganese source compound comprising a member or members selected from the group consisting of manganese salts of $C_1$–$C_{30}$ carboxylic acids, and (b) a phenylenediamine compound having the structure

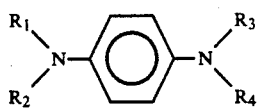

wherein $R_1$, $R_2$, $R_3$, and $R_4$ are the same or different and are hydrogen, $C_1$–$C_{20}$ alkyl, $C_1$–$C_{20}$ aryl, $C_1$–$C_{20}$ alkaryl, or $C_1$–$C_{20}$ aralkyl, with the proviso that at least one of $R_1$, $R_2$, $R_3$, or $R_4$ is hydrogen, the weight ratio of (a):(b), wherein (a) is measured as Mn, being from about 0.05:1 to about 2.5:1.

2. A method as recited in claim 1 wherein the amount of (a) and (b) added, collectively, to the acrylic acid monomer is from about 1–10,000 ppm per one million parts of the monomer.

3. A method as recited in claim 2 wherein the amount of (a) and (b) added, collectively, to the monomer is from about 5–1000 ppm.

4. A method as recited in claim 1 wherein (b) comprises N-phenyl-N'-(1,4-dimethylpentyl)-p-phenylenediamine.

5. A method as recited in claim 1 wherein (a) comprises manganese formate, manganese acetate, manganese propionate, manganese butyrate, or manganese octanoate.

6. A method as recited in claim 1 wherein (a) comprises Mn naphthenate, Mn tallate, and Mn stearate.

7. Acrylic acid anti-polymerization composition comprising a liquid carrier and dissolved or dispersed therein (a) a manganese source compound comprising a member or members selected from the group consisting of manganese salts of $C_1$–$C_{30}$ carboxylic acids, and (b) a phenylenediamine compound having the structure

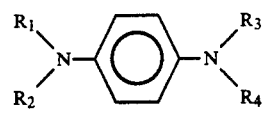

wherein $R_1$, $R_2$, $R_3$, and $R_4$ are the same or different and are hydrogen, $C_1$–$C_{20}$ alkyl, $C_1$–$C_{20}$ aryl, $C_1$–$C_{20}$ alkaryl, or $C_1$–$C_{20}$ aralkyl, with the proviso that at least one of $R_1$, $R_2$, $R_3$, or $R_4$ is hydrogen, the weight ratio of (a):(b), wherein (a) is measured as Mn, being from about 0.05:1 to about 2.5:1.

8. Acrylic acid anti-polymerization composition as recited in claim 7 wherein said liquid carrier comprises a non-polar organic solvent and wherein (a) and (b) are both dissolved in said solvent.

9. Acrylic acid anti-polymerization composition as recited in claim 8 wherein said Mn salts comprise Mn salts of fatty acids soluble in said solvent.

10. Acrylic acid anti-polymerization composition as recited in claim 8 wherein said non-polar solvent comprises heavy aromatic naphtha.

11. Acrylic acid anti-polymerization composition as recited in claim 7 wherein (a) comprises manganese naphthenate and (b) comprises N-phenyl-N'-(1,4-dimethylpentyl)-p-phenylenediamine.

12. Acrylic acid anti-polymerization composition as recited in claim 8 wherein said non-polar organic solvent comprises xylene or heavy aromatic naphtha.

13. Acrylic acid anti-polymerization composition as recited in claim 7 further comprising acrylic acid monomer.

* * * * *